United States Patent
Werbitzky et al.

[11] Patent Number: 6,011,178
[45] Date of Patent: Jan. 4, 2000

[54] PROCESS FOR THE PREPARATION OF 2-AMINO-4,5,3',4'-TETRAMETHOXYBENZOPHENONE

[75] Inventors: Oleg Werbitzky, Visp; Walter Brieden, Brig-Glis; Etienne Heinzmann, Visperterminen, all of Switzerland

[73] Assignee: Lonza, Ltd., Gampel/Valais, Switzerland

[21] Appl. No.: 09/266,741

[22] Filed: Mar. 12, 1999

[30] Foreign Application Priority Data

Mar. 13, 1998 [CH] Switzerland .............................. 0610/98

[51] Int. Cl.[7] ........................ C07C 217/84; C07C 217/90
[52] U.S. Cl. .......................... 564/328; 564/329; 564/321; 564/416; 568/306; 568/314; 568/332; 568/333
[58] Field of Search ..................................... 568/306, 319, 568/322, 332, 333, 312, 314, 315; 564/416, 321, 328, 329

[56] References Cited

U.S. PATENT DOCUMENTS 5,650,410  7/1997  Sohda et al. ........................ 514/233.8

FOREIGN PATENT DOCUMENTS 06328859  5/1993  Japan .
WO 97-09984  3/1997  WIPO .

OTHER PUBLICATIONS

Lawson et al, J.Chem.Soc., vol. 125, p. 626, 1924.
Harrison et al, Compendium of Organic Synthetic Methods, p. 266, 1971.

March, Advanced Organic Chemistry, third edition, p. 486, 1985.

Munchhof et al., Journal Of Organic Chemistry, vol. 60, No 23, (Nov. 3, 1995), pp. 7086 and 7087, (Munchhof et al.).

Upton et al., Journal Of Pharmacy and Pharmacology, vol. 50, No. 5, May, 1998, pp. 476 yo 482, (Upton et al.).

Primary Examiner—Gary Geist
Assistant Examiner—Sreeni Padmanabhan
Attorney, Agent, or Firm—Fisher, Christen & Sabol

[57] ABSTRACT

2-Amino-4,5,3',4'-tetramethoxybenzophenone of the formula:

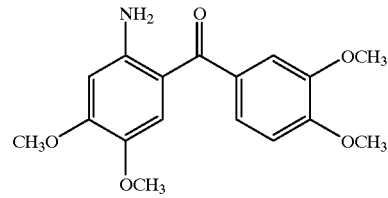

is prepared by mononitration of 3,3',4,4'-tetramethyoxybenzophenone using nitric acid in the presence of acetic acid, and subsequent reduction of the nitro group. The compound is an intermediate in the synthesis of active ingredients against rheumatoid arthritis.

9 Claims, No Drawings

PROCESS FOR THE PREPARATION OF 2-AMINO-4,5,3',4'-TETRAMETHOXYBENZOPHENONE

BACKGROUND OF THE INVENTION

1. Field of the Invention

The invention relates to a process for the preparation of 2-amino-4,5,3',4'-tetramethoxybenzophenone of the formula:

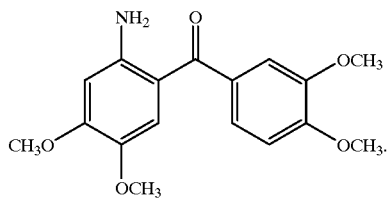

I

2. Background of the Invention

2-Amino-4,5,3',4'-tetramethoxybenzophenone of the formula I is an important intermediate in the synthesis of quinoline derivatives, which are of importance as pharmaceutical active ingredients against rheumatoid arthritis (European Published Patent Application No. 0567107, European Published Patent Application No. 0608870, European Published Patent Application No. 0634169, European Published Patent Application No. 0686630, International Published Patent Application No. WO 95/24394 and International Published Patent Application No. WO 97/09984). However, a process for the preparation of this compound has not hitherto been published.

BROAD DESCRIPTION OF THE INVENTION

The object of the invention is to provide a process for the preparation of 2-amino-4,5,3',4'-tetramethoxybenzophenone which can be carried out on an industrial scale. The object of the invention is achieved by the process of the invention.

Surprisingly, it has been found that the desired product is obtainable in good yield by selective (mono)nitration of 3,3',4,4'-tetramethoxybenzophenone of the formula:

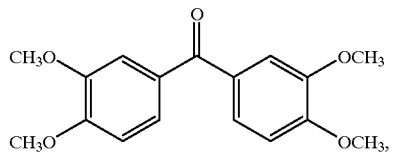

II using nitric acid in the presence of acetic acid to 2-nitro-4,5,3',4'-tetramethoxybenzophenone of the formula:

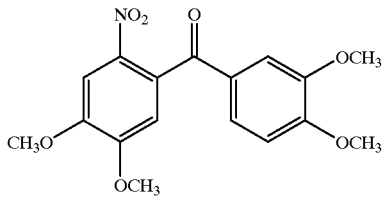

III and subsequent selective reduction of the nitro group. This synthesis is surprising because it is known that in the nitration of 3,3',4,4'-tetramethoxybenzophenone using nitric acid under customary conditions, dinitration to 2,2'-dinitro-4,5,4',5'-tetramethoxybenzophenone takes place in virtually quantitative yield (W. Lawson et al., *J. Chem. Soc.* 1924, 125, 626). In the presence of acetic acid, however, the mononitrated product 2-nitro-4,5,3',4'-tetramethoxybenzophenone (III) is obtained with high selectivity. This novel compound is likewise provided by the present invention.

DETAILED DESCRIPTION OF THE INVENTION

The nitration is preferably carried out using 65 percent strength ("concentrated") nitric acid in acetic acid ("glacial acetic acid") as the solvent at from 0° to 40° C. A particularly preferred reaction temperature is from 10° to 30° C.

The reduction of the nitro group in III to the amino group can take place under customary conditions, for example, using tin and hydrochloric acid. Only conditions under which the keto group would be expected to undergo reduction must be avoided.

The reduction is preferably carried out by catalytic hydrogenation.

A particularly preferred catalyst for the catalytic hydrogenation is a supported platinum catalyst, in particular platinum on activated carbon.

The preparation of 3,3',4,4'-tetramethoxybenzophenone is known from the literature and is usually carried out by Friedel-Crafts acylation of 1,2-dimethoxybenzene using 3,4-dimethoxybenzoyl chloride (W. Lawson et al., loc. cit.). Another known synthesis of this compound proceeds via the condensation of oxalyl chloride with 1,2-dimethoxybenzene (H. Staudinger et al., *Helv. Chim. Acta.* 1921, 4, 334). Both of the known syntheses use carbon disulfide as the solvent and stoichiometric amounts of aluminum chloride as the catalyst and are, therefore, unsuitable for large-scale production for reasons of safety and because of the large amounts of waste material.

Surprisingly, it has been found that when polyphosphoric acid is used as the catalyst, 1,2-dimethoxybenzene (veratrole) can be acylated directly using 3,4-dimethoxybenzoic acid (veratric acid). The advantages of this reaction are the ready availability of the starting materials coupled with a high yield and very simple product isolation. After water has been added, the 3,3',4,4'-tetramethoxybenzophenone can be isolated by simple filtration.

The examples below illustrate how the process according to the invention is carried out but are not intended to impose any limitation.

EXAMPLE 1

3,3',4,4'-Tetramethoxybenzophenone 16.92 g (120 mmol) of 1,2-dimethoxybenzene and 22.08 g (120 mmol) of 3,4-dimethoxybenzoic acid were stirred in 100 g of polyphosphoric acid (d=2.1 g/ml) at 80° C. for 30 min. The reaction mixture was then cooled to 60° C., and 250 ml of water was added dropwise over the course of 30 min. The resulting mixture was further cooled using ice, and the resulting precipitate was filtered off, washed with 2×60 ml of water and finally dried under reduced pressure to give 35.7 g of a reddish product. The yield of the product was 98 percent of theory.

EXAMPLE 2

2-Nitro-4,5,3',4'-tetramethoxybenzophenone

A mixture of 2.93 g (9.7 mmol) of 3,3',4,4'-tetramethoxybenzophenone (prepared according to Example 1), 9 g of glacial acetic acid and 1.88 g (19.4 mmol) of 65 percent strength nitric acid was stirred at room temperature for 7.5 h. 22 ml of water was then added dropwise, and the resulting precipitate was filtered off, washed 2×6 ml of water and dried to give 2.41 g of a beige solid. The yield of the product was 71.5 percent of theory. Further data concerning the product was:

$^1$H NMR (CDCl$_3$, 400 MHz): δ=7.72(s, 1H); 7.59(d, J=2.1 Hz, 1H); 7.05(dd, J=8.4/2.1 Hz, 1H); 6.85(s, 1H); 6.78(d, J=8.4 Hz, 1H); 4.03(s, 3H); 3.97(s, 3H); 3.95(s, 3H); 3.92(s, 3H). $^{13}$C NMR ("off resonance", CDCl$_3$, 100 MHz): δ=192(s); 153.9(s); 153.8(s); 149.6(s); 149.5(s); 139.6(s); 130.6(s); 129.5(s); 124.5(d); 110.4(d); 110.1(d); 110.1(d); 106.9(d); 56.7(q); 56.6(q); 56.1(q); 56.1(q).

EXAMPLE 3

2-Amino-4,5,3',4'-tetramethoxybenzophenone

In 10 ml of ethanol, 1 g (2.88 mmol) of 2-nitro-4,5,3',4'-tetramethoxybenzophenone (prepared according to Example 2) was hydrogenated on 100 mg of platinum/activated carbon (5 percent Pt, moist, H$_2$O content 50 percent) at 40° C. and a hydrogen pressure of 2 bar. After 5 h, the reaction mixture was cooled to room temperature, and 10 ml of acetonitrile was added. The catalyst was filtered off, and the filtrate was evaporated under reduced pressure to give 0.88 g of 2-amino-4,5,3',4'-tetramethoxybenzophenone as a beige solid. The yield of the product was 96 percent of theory.

What is claimed is:

1. A process for the preparation of 2-amino-4,5,3',4'-hoxybenzophenone of formula:

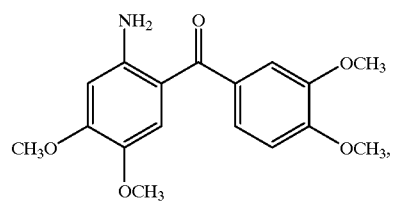

characterized in that, in a first stage, 3,3',4,4'-tetramethoxybenzophenone of formula:

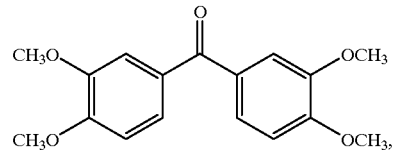

is nitrated using nitric acid in the presence of acetic acid to 2-nitro-4,5,3',4'-methoxybenzophenone of formula:

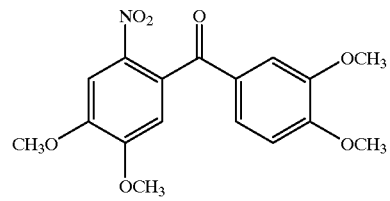

and, in a second stage, the 2-nitro-4,5,3',4'-tetramethoxybenzophenone of formula III is reduced to the 2-amino-4,5,3',4'-tetramethoxybenzophenone of formula I.

2. The process according to claim 1, wherein the nitration is carried out using 65 percent strength nitric acid in acetic acid as solvent at from 0° to 40° C.

3. The process according to claim 1, wherein the reduction takes place by catalytic hydrogenation.

4. The process according to claim 2, wherein the reduction takes place by catalytic hydrogenation.

5. The process according to claim 3, wherein the catalytic hydrogenation is carried out on a supported platinum catalyst.

6. The process according to claim 4, wherein the supported platinum catalyst used is platinum on activated carbon.

7. A process for the preparing of 3,3',4,4'-tetramethoxybenzophenone of formula:

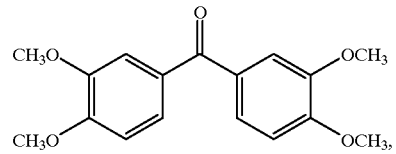

comprising acylating 1,2-dimethoxybenzene using 3,4-dimethoxybenzoic acid in the presence of polyphosphoric acid.

8. 2-Nitro-4,5,3',4'-tetramethoxybenzophenone of formula:

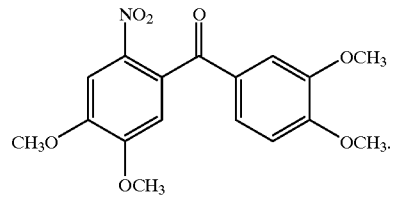

9. A process for the preparation of 2-amino-4,5,3',4'-tetramethoxybenzophenone of formula:

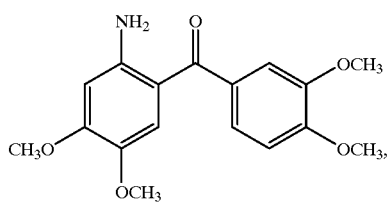

comprising, in a first stage, acylating 1,2-dimethoxybenzene using 3,4-dimethoxybenzoic acid in the presence of polyphosphoric acid to provide 3,3',4,4'-tetramethoxybenzophenone of formula:

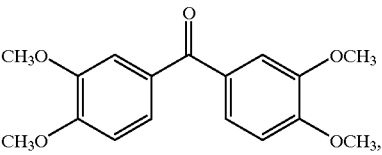

in a second stage, nitrating the 3,3',4,4'-tetramethoxybenzophenone of formula II using nitric acid in the presence of acetic acid to 2-nitro-4,5,3',4'-tetramethoxybenzophenone of formula:

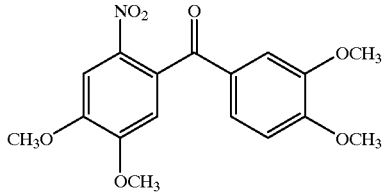

and, in a third stage, reducing the 2-nitro-4,5,3',4'-tetramethoxybenzophenone of formula III to the 2-amino-4,5,3',4'-tetramethoxybenzophenone of formula I.

* * * * *